(12) United States Patent
Nukui

(10) Patent No.: US 6,980,622 B2
(45) Date of Patent: Dec. 27, 2005

(54) METHOD AND APPARATUS FOR IMAGE RECONSTRUCTION AND X-RAY CT IMAGING APPARATUS

(75) Inventor: Masatake Nukui, Tokyo (JP)

(73) Assignee: GE Global Systems Global Technology Company, LLC, Waukesha, WI (US)

(*) Notice: Subject to any disclaimer, the term of this patent is extended or adjusted under 35 U.S.C. 154(b) by 69 days.

(21) Appl. No.: 10/817,222

(22) Filed: Apr. 2, 2004

(65) Prior Publication Data

US 2004/0234022 A1 Nov. 25, 2004

(30) Foreign Application Priority Data

Apr. 3, 2003 (JP) .............................. 2003-100668

(51) Int. Cl.[7] .............................................. A61B 6/03
(52) U.S. Cl. ........................... 378/4; 378/901; 382/131
(58) Field of Search .................... 378/4, 15, 901

(56) References Cited

U.S. PATENT DOCUMENTS

| | | |
|---|---|---|
| 4,590,558 A | 5/1986 | Glover et al. |
| 4,920,491 A | 4/1990 | Eberhard et al. |
| 5,243,664 A | 9/1993 | Tuy |
| 5,933,471 A | 8/1999 | Kalvin |
| 6,094,467 A | 7/2000 | Gayer et al. |
| 6,108,575 A * | 8/2000 | Besson ...................... 600/425 |
| 6,125,193 A | 9/2000 | Han |
| 6,201,888 B1 | 3/2001 | Kalvin |
| 6,292,578 B1 | 9/2001 | Kalvin |
| 6,351,514 B1 * | 2/2002 | Besson ...................... 378/15 |
| 6,650,726 B2 | 11/2003 | Sembritzki et al. |

FOREIGN PATENT DOCUMENTS

JP 2000-083946 3/2000

OTHER PUBLICATIONS

Laigao Chen et al: "Novel method for reducing high-attenuation object artifacts in CT reconstructions", Feb. 24, 2002, pp. 841–850, vol. 4684–ISSN: 0277-786X.

Klotz et al: "Algorithms for the Reduction of CT Artefacts Caused by Metallic Implants", Feb. 2002, pp. 642–650, vol. 1234–ISSN: 0277-786X, Bellingham, VA.

International Search Report, EP Office, 3 pages, Mar. 11, 2004.

* cited by examiner

Primary Examiner—David V Bruce
(74) Attorney, Agent, or Firm—Carl B. Horton, Esq.; Armstrong Teasdale LLP (57) ABSTRACT

A method for decreasing the streak artifact in the reconstructed image due to the existence of foreign matter of high X-ray absorption rate such as metals. The method includes separating discrete region containing the data having abrupt change of value the projection data in the sequential order of radiographic detector elements, transforming the data to continuous data such that the value gradually smoothly changes, filtering the continuous data, composing the filtered data with the data of the discrete regions to form the projection data used for the image reconstruction.

16 Claims, 6 Drawing Sheets

METHOD AND APPARATUS FOR IMAGE RECONSTRUCTION AND X-RAY CT IMAGING APPARATUS

CROSS REFERENCE TO RELATED APPLICATIONS

This application claims the benefit of Japanese Application No. 2003-100668 filed Apr. 3, 2003.

BACKGROUND OF THE INVENTION

The present invention is related to a radiological tomographic imaging apparatus such as an X-ray CT (computed tomography).

The X-ray CT includes a beam emitter system and detector system, i.e., X-ray emitter system and detector system, which are opposedly placed at both sides of a subject, and are rotated about the subject while emitting an X-ray beam to the subject (scanning). The X-ray beam transmitted through the subject is detected by the detector system around the subject in a plurality of view directions to measure the data projected through the subject by the X-ray beam in each direction. A tomographic image of the subject can be reconstructed based on the projected data.

To obtain a tomographic image, the projection data from the subject may be preprocessed, and thus preprocessed projection data may be used to reconstruct an image according to for example a filtered back projection method.

In the filtered back projection method, projection data of the subject will be filtered as needed for image reconstruction and the filtered projection data will be back projected to reconstruct an image.

In the filtering, a variety of filters can be selected according to the diagnostic purpose and the subject lesion. The filtering consists of FFT (fast Fourier transfer) of the data, multiplication by the selected filter with the FFT data, and IFFT (inverse FFT). In addition, high frequency noises in the projection data may be eliminated during the filtering. The noise reduction technique on high frequency noises included in the projection data can be seen for example in Patent Document 1:

[Patent Document 1]
JP-A-2000-83946

When there exists a foreign matter that is different from the components of a human body, such as metals, in the subject, the value in the detected projection data in the part corresponding to the foreign matter may abruptly change, to become a part noncontinuous from other parts. This is because the X-ray absorption rate of metals is very high.

In case in which projection data including the image of foreign matter such as a metal is filtered, data value of the part including the foreign matter may contain high frequency components, which value may abruptly change. The data value in this part may become changed so that the projection data after the inverse FFT may have some distortion such as undershoot and overshoot.

There is a disadvantage that if the projection data having such distortion is used to back projection to reconstruct an image, streak artifact may be occurred in the image part corresponding to the foreign matter such as metals.

SUMMARY OF THE INVENTION

Therefore, an object of the present invention is to provide a method and apparatus for image reconstruction and X-ray CT imaging apparatus, allowing decreasing the streak artifact in the reconstructed image due to the existence of foreign matter of high X-ray absorption rate such as metals.

The image reconstruction apparatus in accordance with the present invention uses the projection data obtained by detecting the radiation beam transmitted through a subject with a plurality of radiation beam detector elements to reconstruct the tomographic image of the subject, which apparatus incorporates a noncontinuous data processing means, for performing a predetermined filtering to data except for any discrete area including data of noncontinuous value, among the projection data arranged in the order of sequence of said radiation beam detector elements array, to reassemble said noncontinuous data of discrete area with the data having said filtering undergone to provide the projection data for reconstructing said tomographic image.

Preferably, said noncontinuous data processing means includes: a separator means for isolating any noncontinuous data in said discrete area from said projection data, converting said isolated noncontinuous projection data to continuous data so as for the value to change consistently, and serving only those continuous data for said filtering; and a synthesizer means for synthesizing said continuous data derived from said filtering and said noncontinuous data of discrete area to reassemble the projection data to be provided to said image reconstruction means.

It can be conceivable that the image reconstruction apparatus may comprise said noncontinuous data processing means, composed of: an extractor means, for extracting said discrete areas based on the difference between the projection data having said filtering undergo and the projection data not having said filtering undergo; and a synthesizer means for substituting the extracted noncontinuous data of said discrete area in the projection data having said filtering undergo with the projection data not having the filtering to prepare the projection data to be provided to said image reconstructor means.

An image reconstruction method in accordance with the present invention, uses the projection data obtained by detecting the radiation beam transmitted through a subject with a plurality of radiation beam detector elements to reconstruct the tomographic image of said subject, which method comprises: a step for performing a predetermined filtering to data except for any discrete area including data of noncontinuous value, among the projection data arranged in the order of sequence of said radiation beam detector elements array, to reassemble said noncontinuous data of discrete area with the data having said filtering undergone to provide the projection data for reconstructing said tomographic image.

A radiographic tomography imaging apparatus in accordance with the present invention, may comprise: a radiation detector, having a radiation emitter means and a plurality of radiation detector elements placed opposedly on the both sides of a subject; and an image reconstruction apparatus, for reconstructing a tomographic image of said subject based on the projection data obtained by detecting the radiation transmitted through said subject by said plurality of radiation detector elements; in which said image reconstruction apparatus comprises a noncontinuous data processing means, for performing a predetermined filtering to data except for any discrete area including data of noncontinuous value, among the projection data arranged in the order of sequence of said radiation beam detector elements array, to reassemble said noncontinuous data of discrete area with the data having said filtering undergone to provide the projection data for reconstructing said tomographic image.

In accordance with the present invention, during the filtering performed prior to the reconstruction of tomographic image from the projection data, any noncontinuous data included in the projection data may be used as is without filtering. The high frequency component contained in the noncontinuous data thereby may not be distorted, resulting in a more accurate reconstruction of an image in the noncontinuous parts.

In accordance with the present invention, a method and apparatus of image reconstruction and a radiographic tomography imaging apparatus are provided, which allows decreasing the streak artifact developed in the reconstructed image due to the existence of a foreign matter, such as a metal in the subject, which has a high X-ray absorption rate.

Further objects and advantages of the present invention will be apparent from the following description of the preferred embodiments of the invention as illustrated in the accompanying drawings.

DETAILED DESCRIPTION OF THE INVENTION

A detailed description of one preferred embodiment embodying the present invention will now be given referring to the accompanying drawings.

[First Embodiment]

Figure 1:
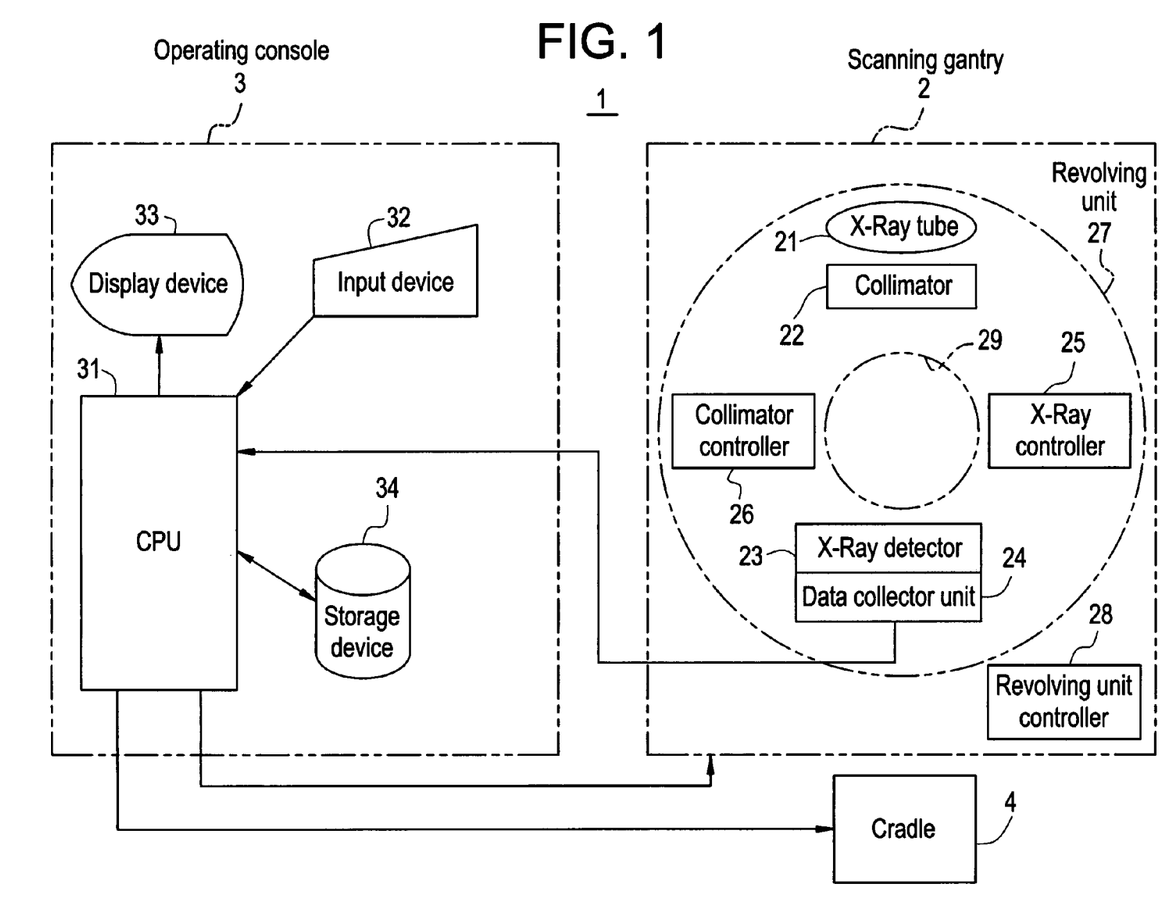
FIG. 1 is a schematic block diagram illustrating an overview of an X-ray CT apparatus as a preferred embodiment of a radiographic tomography imaging apparatus in accordance with the present invention.

Now referring to FIG. 1, there is shown a schematic block diagram illustrating an overview of an X-ray CT apparatus as a preferred embodiment of a radiographic tomography imaging apparatus in accordance with the present invention.

As shown in FIG. 1, The X-ray CT 1 may have a scanning gantry 2, an operating console 3, and an imaging table (cradle) 4.

The scanning gantry 2 may include an X-ray tube 21. The X-ray tube 21 may emit an X-ray beam not shown in the figure, which passes through a collimator 22, which shapes the beam into an X-ray beam of sector form to be incident into an X-ray detector 23.

The X-ray detector 23 may include a plurality of X-ray detector elements, arranged as an array oriented in the direction of sector of fan beam. The X-ray detector 23 may be a multichannel detector having a plurality of X-ray detecting elements arranged in an array.

The X-ray detector 23 may form an X-ray incident plane of cylindrical concave shape. The X-ray detector 23 may be formed for example by a combination of scintillator and photodiode. The X-ray detector in accordance with the present invention may not be intended to be limited thereto, any other forms of detectors can be used instead, such as semiconductor X-ray detector elements using for example Cadmium-Tellurium (CdTe), or an ion chamber type X-ray detector elements using Xenon (Xe) gas.

The X-ray detector 23 is connected to a data collector unit 24. The data collector unit 24 is used to gather detected data from each X-ray detector element. The emission of X-ray from the X-ray tube 21 is controlled by an X-ray controller 25. The connection between the X-ray tube 21 and the X-ray controller 25 as well as the connection between the collimator 22 and a collimator controller 26 are not depicted in the figure. The collimator 22 is controlled by the collimator controller 26.

A revolving unit 27 of the scanning gantry 2 incorporates the X-ray tube 21, the collimator 22, the X-ray detector 23, the data collector unit 24, the X-ray controller 25 and the collimator controller 26. The subject to be images will be carried on a cradle in a bore 29 located in the center of the revolving unit 27. The revolving unit 27 will rotate under the control of a revolving unit controller 28, emit X-ray beam from the X-ray tube 21, and detect the X-ray beam transmitted through the subject at the X-ray detector 23 as the projection information for each view. The connection between the revolving unit 27 and the revolving unit controller 28 is not shown in the figure.

The operation console 6 may have a central processing unit (CPU) 31, an input device 32, a display device 33, and a storage device 34.

The CPU 31 and the storage device 34 constitute the image reconstructing apparatus in accordance with the present invention.

The CPU 31 consists of for example a microprocessor and a memory.

The CPU 31 may have at least the function of controlling the operation of the scanning gantry 2 to collect the projection data obtained by detecting the X-ray transmitted through the subject by the X-ray detector 23, and the function of reconstructing a tomographic image of the subject based on thus collected X-ray projection data, in accordance with the software stored in the storage device 34.

The data collected at the data collector unit 24 will be input into the CPU 31 via a data collector buffer not shown in the figure, and the CPU 31 in turn uses the collected projection data to reconstruct an image. The image reconstruction processing by the CPU 31 will be described in greater details later.

To the CPU 31 are connected the display device 33 and the input device 32. The display device 33 displays information such as information on the tomographic image and any other information output from the CPU 31. The input device 32 is manipulated by an operator to input to the CPU 31 various instructions and information. The operator will use the display device 33 and the input device 32 to operate the apparatus interactively.

In the X-ray CT 1 as have been described above, The X-ray tube 21 and the X-ray detector 23 are relatively moving in the scanning gantry 2 to scan the area to be imaged in the subject to collect the projection data of the subject in the data collector unit 24, and the projection data will be sent to the CPU 31, which in turn a tomographic image of the subject will be reconstructed.

Figure 2:
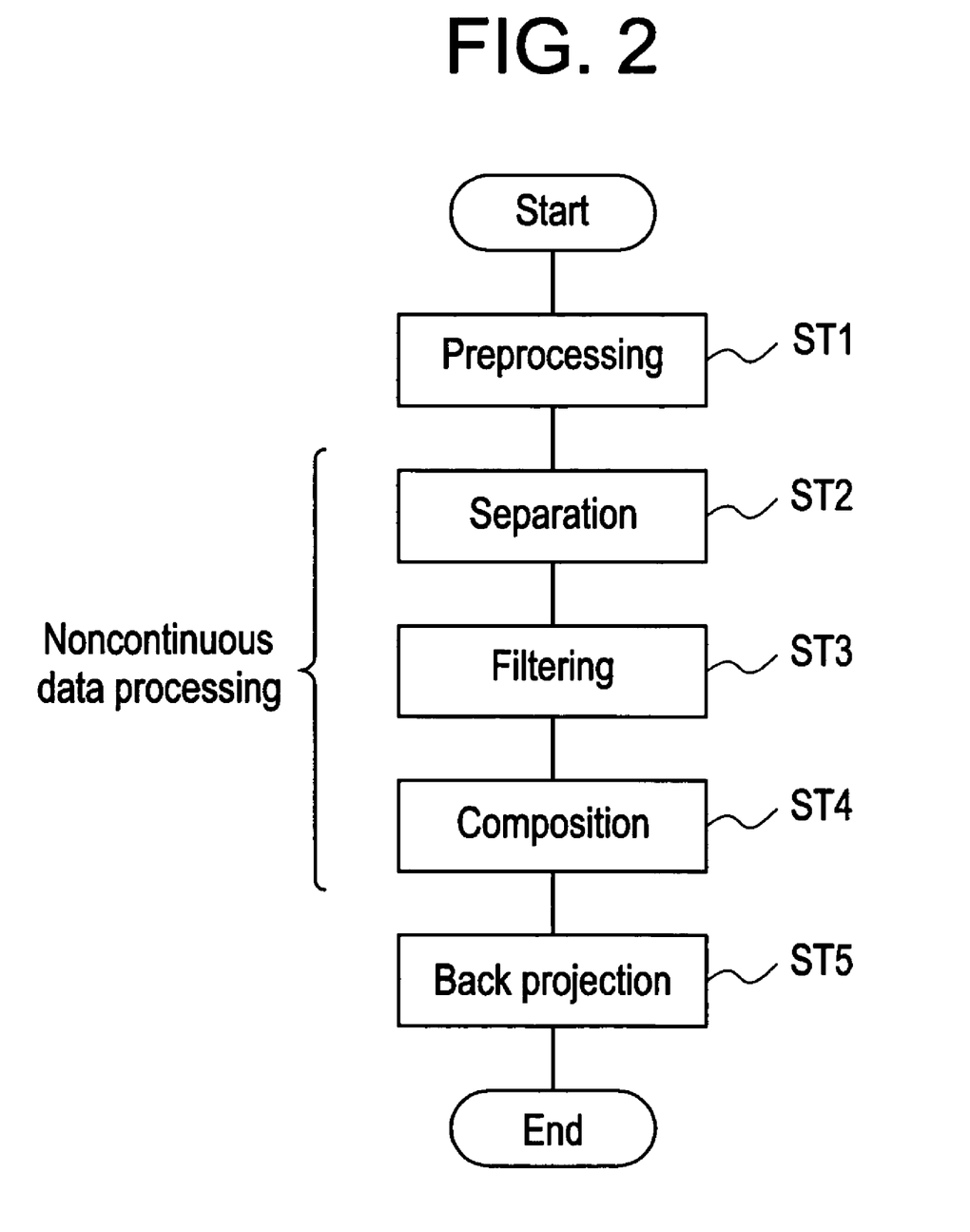
FIG. 2 is a schematic diagram illustrating an overview of an image reconstruction procedure take by the central processing unit.

Now referring to FIG. 2, there is shown an overview of an image reconstruction procedure take by the CPU 31.

The image reconstruction by the CPU 31 may be conducted according to the filtered back projection method. The filtered back projection method itself is well known in the art and the detailed description thereof will be omitted.

As shown in FIG. 2, the image reconstruction by the CPU 31 may be composed of the noncontinuous data processing, consisted of preprocessing (step ST1), separation (step ST2), filtering (step ST3), and synthesis (step ST4), and of the back projection processing (step ST5).

In the preprocessing (step ST1), the projection data of the subject obtained from the data collector unit 24 are to be compensated for physically and electrically so as to reconstruct a normal image.

Now referring to FIG. 3, there is shown a schematic diagram illustrating the details of separation process (step ST2). In the figure, (a) illustrates an exemplary projection data of the subject obtained from the data collector unit 24, (b) illustrates the projection data after separation performed, and (c) illustrates noncontinuous data isolated. The data is in the sequence (order) of channel of the detector array in the X-ray detector 23.

The noncontinuous data herein is indicative of part of data that contains data that the value is different over a plurality of channels.

Figure 3A:
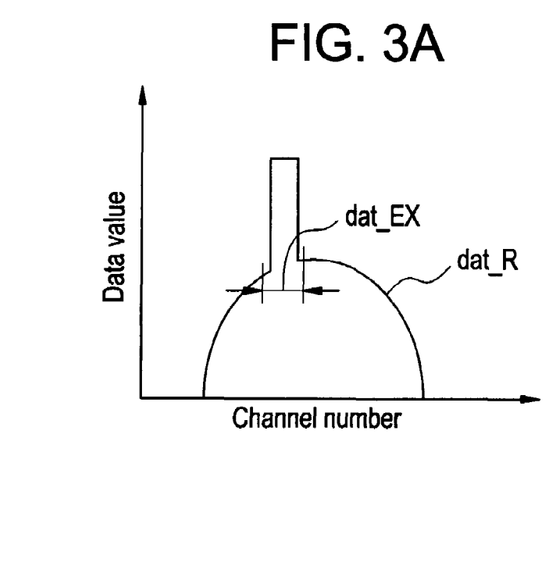
FIG. 3 is a schematic diagram illustrating the details of separation process.

For example, when a foreign matter within the subject exists, such as metals, which exhibits a high absorption rate of X-ray different from the absorption rate of human body, as shown in FIG. 3(a), the data value of the part corresponding to the foreign matter may abruptly changes, in the projection data dat_R. In the part of data dat_R that corresponds to where no foreign matter exists, data value changes continuously and smoothly.

Now defining noncontinuous data dat_EX as the data from the discrete region that contains abruptly changing data value, in the projection data dat_R shown in FIG. 3(a), the noncontinuous data dat_EX may contain high frequency components when considering data value in the frequency domain.

In any other regions except for the noncontinuous data dat_EX, such high frequency components are not found since the data value moves gradually smoothly.

If filtering every projection data dat_R in order to remove the high frequency noise components contained in the projection data dat_R, the high frequency components contained in the noncontinuous data dat_EX also may be removed.

Figure 3B:
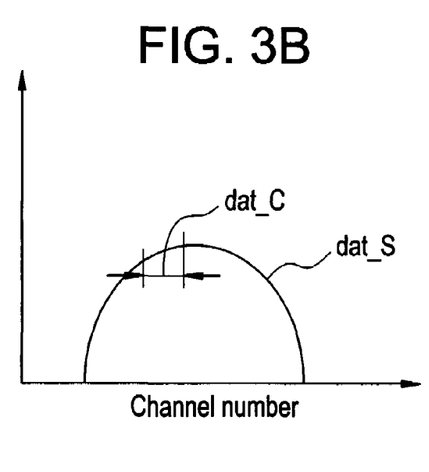
Figure 3C:
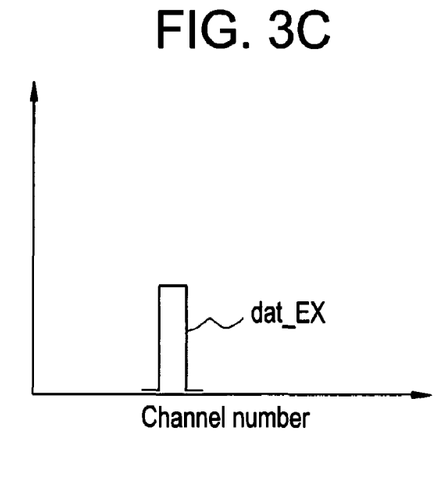

For that reason, in the separation processing (step ST2), noncontinuous data dat_EX will be isolated from the projection data dat_R, as shown in FIG. 3(c).

In the projection data dat_R after separating the noncontinuous data dat_EX where the noncontinuous data dat_EX has resided may be completed as shown in FIG. 3(b), with the data dat_C. More specifically, data around the noncontinuous data dat_EX may be used for interpolation to fit the data region.

In this manner a continuous data dat_S can be yielded, in which data value changes gradually smoothly in every regions.

The continuous data dat_S may be used for the filtering.

In the filtering (step ST3), at first the continuous data dat_S will be processed with FFT (fast Fourier Transform).

Then, the data will be filtered with a filter selected according to the diagnosis purpose or subject lesion.

Thereafter, thus filtered continuous data dat_S will be recovered by the IFFT inverse FFT).

The filter used in the filtering (step ST3) may be appropriately selected so as to be best suited to the diagnostic purpose and lesion to be imaged, however the filter will eliminate the high frequency noise components contained in the continuous data dat_S, at the same time.

Now referring to FIG. 4, there is shown a graph illustrating the filter characteristics in the filtering (step ST3), where (a) is data prior to FFT, and (b) data after IFFT.

Figure 4A:
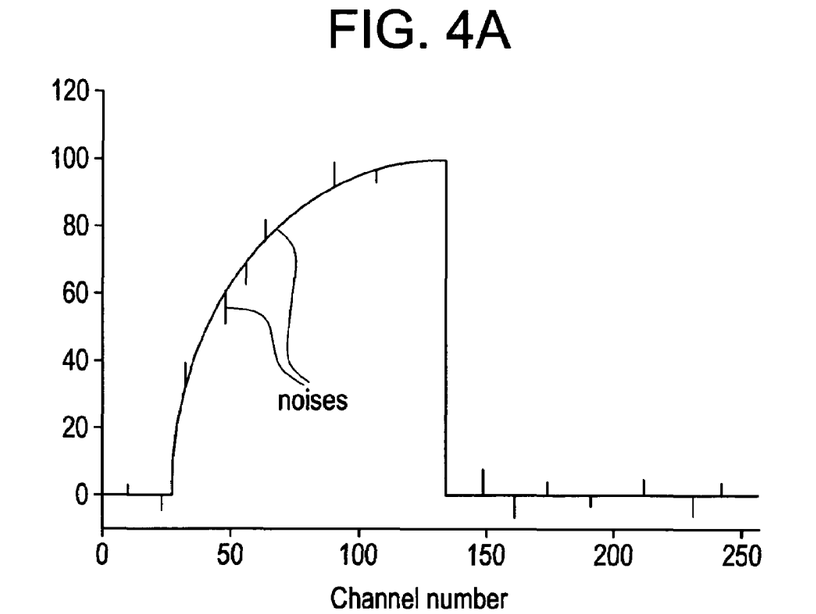
FIG. 4 is a graph illustrating the filter characteristics in the filtering.

It can be seen from FIG. 4(a), that noise, which exists in the data prior to FFT, is eliminated by the filtering.

Figure 4B:
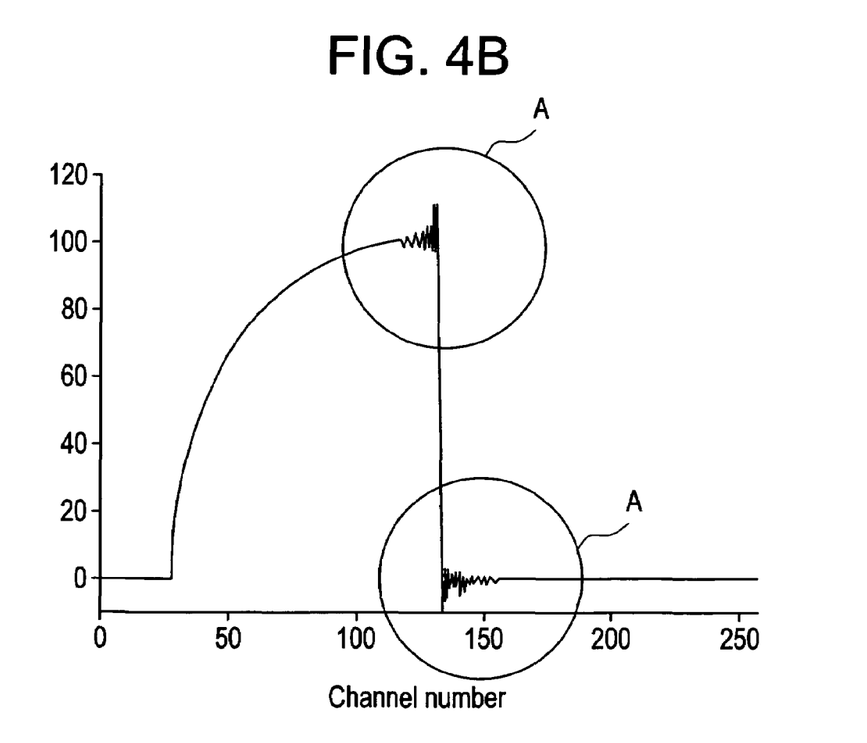

In addition, if a region of abrupt change of value exists in the data, such distortion of data as overshoot or undershoot, as shown in the circle A of FIG. 4(b), will be developed around the region in the data after IFFT.

In accordance with this embodiment, in the separation processing (step ST2) described above, noncontinuous data dat_EX containing high frequency components is isolated so as to exclude from the object data to be processed. Any noises in the continuous data dat_S thereby will be removed by the filtering while at the same time no distortion occurs.

The synthesis (step ST4) combines the isolated noncontinuous data dat_EX and the filtered continuous data dat_S. Thus combined data will be served as data used for the image construction by the back projection (step ST5).

As have been described above, in this preferred embodiment, only the continuous data dat_S obtained by isolating the noncontinuous data dat_EX contained in the projection data dat_R are subject to filter. Then thus filtered continuous data dat_S is composed with the noncontinuous data dat_EX. This composite data is used for the back projection. The streak artifacts caused by the eliminating process of the high frequency components in the filtering process in the reconstructed image is unlikely to happen, so that the tomographic image containing a foreign matter such as a metal that has a high X-ray absorption rate will be facilitated to reconstruct.

[Second Embodiment]

Figure 5:
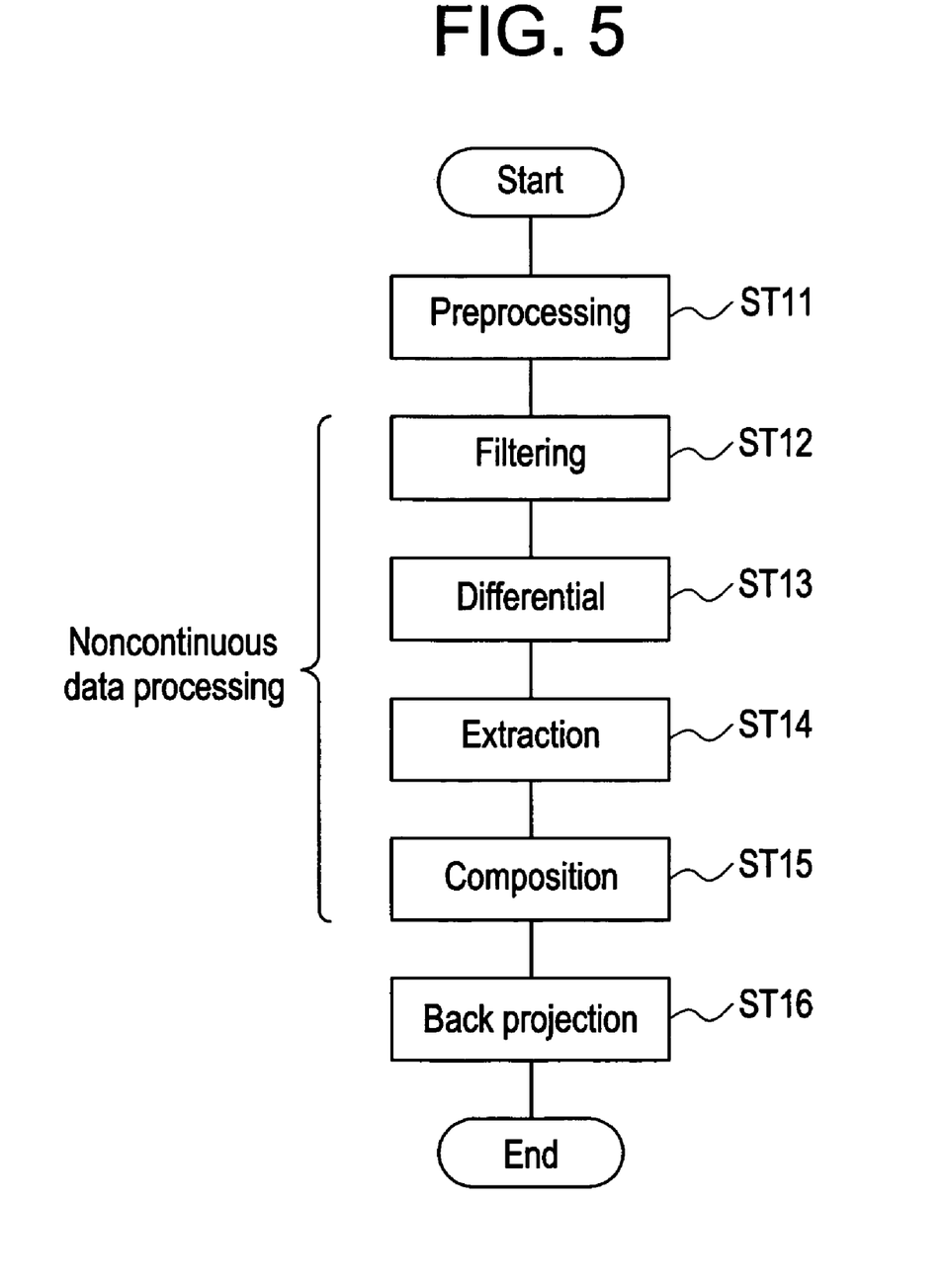
FIG. 5 is a schematic diagram illustrating an overview of image reconstruction process in accordance with another preferred embodiment of a radiographic tomography imaging apparatus of the present invention.

Now referring to FIG. 5, there is shown an overview of image reconstruction process in accordance with another preferred embodiment of a radiographic tomography imaging apparatus of the present invention.

It is to be noted here that the image reconstruction procedure of the present embodiment is just similar to that described in the previous embodiment, except for the process performed by the CPU 31.

As shown in FIG. 5, the image reconstruction process performed by the CPU 31 in accordance with the preferred embodiment may be composed of noncontinuous data processing consisted of preprocessing (step ST11), filtering (step ST12), differentiation (step ST13), extraction (step ST14), and composition (step ST15), and of the back projection (step ST16).

The preprocessing (step ST11) is just similar to that performed in the first preferred embodiment.

In the filtering (step ST12), the processing is identical to that performed in the first preferred embodiment. More specifically, FFT (fast Fourier transform) is done on the projection data of the subject obtained from the data collector unit 24, then filtering with a filter selected according to the diagnostic purpose or object lesion, and finally recovering by IFFT (inverse fast Fourier transform) on the filtered data.

Now referring to FIG. 6, there is shown (a) an exemplary projection data prior to filtering, (b) an exemplary projection data after filtering, and (c) differential of projection data before and after the filtering.

Figure 6A:
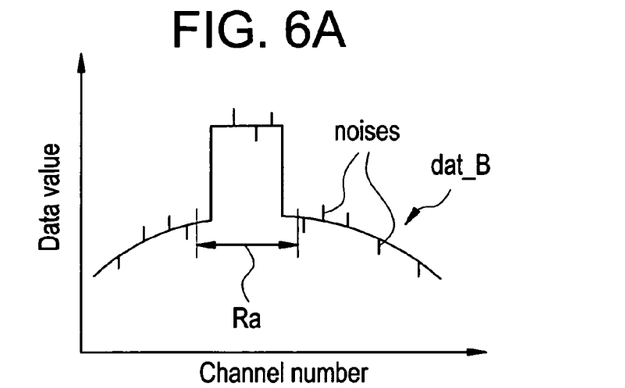
FIG. 6 is a graph illustrating an exemplary projection data before filtering, after filtering, and the differential before and after the filtering.

As shown in FIG. 6(a), the projection data dat_B before filtering contains some noises, as well as a discrete region Ra that has data values noncontinuously changing. As have been described previously this discrete region Ra may be resulted from the existence of a foreign matter, such as a metal, which has a high X-ray absorption rate.

Figure 6B:
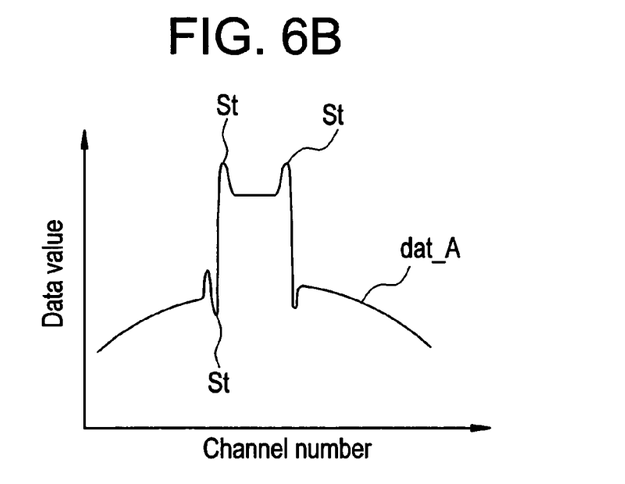

Filtering the projection data dat_B shown in FIG. 6(a), will result in, for example, data dat_A as shown in FIG. 6(b).

It can obviously be seen in the data dat_A after filtering as shown in FIG. 6(b) that distortion st is developed at the location in the noncontinuous region Ra where the data value is abruptly moving.

Next, the differential processing (step ST13) may compute the differential between the projection data dat_B before filtering and projection data dat_A after filtering. The differential data, as shown in FIG. 6(c), may include noises contained in the projection data dat_B and distortion st developed by the filtering.

Figure 6C:
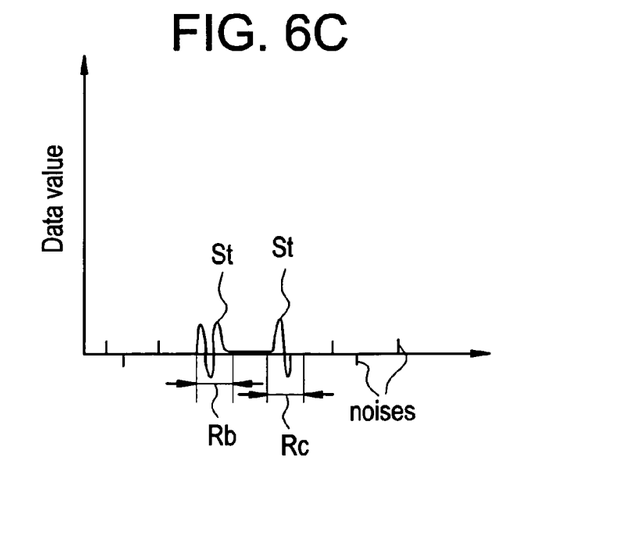

Then the extraction processing (step ST14) may extract from the differential data as shown in FIG. 6(c) discrete regions Rb and Rc. Those discrete regions Rb and Rc are regions in the projection data dat_B where the distortion st can be developed by the filtering.

These discrete regions Rb and Rc can be extracted by defining a threshold and comparing the differential data with the predetermined threshold. It is important to note that the noises should have to be distinguished from the distortion st when comparing the differential data with the threshold. The distortion st exists over a plurality of channels, while on the other hand noises are likely to develop in a single channel. Since the signal level of the distortion st is different from the level of noises, the distinction between them may be easy.

In the composition (step ST15), the data in the discrete regions Rb and Rc extracted by the extraction step (step ST14) from within the projection data dat_A after filtering, will be substituted with the projection data dat_B before filtering. In other words, data with no distortion st developed is used for replacing the discrete regions Rb and Rc. The data thus composed is used for the image reconstruction by the back projection (step ST16).

As can be appreciated from the foregoing description, in the present embodiment, by deliberately developing distortion st by filtering the projection data dat_B, the discrete regions Rb and Rc are identified. For the data actually used for the image reconstruction, data without filtering is applied to the discrete regions Rb and Rc. In this manner the streak artifacts caused by the filtering may be positively prevented from developing in the image reconstructed after the back projection.

Although in the above description exemplary embodiments have been depicted which uses X-ray beam as radiation, the radiation may not be limited thereto. For example any radiation including the gamma ray can be used instead. At the present time of writing the X-ray is the most preferable because of its widest assortment of practical means with respect to the generation, detection and control.

Many widely different embodiments of the invention may be configured without departing from the spirit and the scope of the present invention. It should be understood that the present invention is not limited to the specific embodiments described in the specification, except as defined in the appended claims.

What is claimed is:

1. An image reconstruction apparatus, which uses the projection data obtained by detecting the radiation beam transmitted through a subject with a plurality of radiation beam detector elements to reconstruct the tomographic image of said subject, comprising:

a noncontinuous data processing device, for performing a predetermined filtering to data except for any discrete area including data of noncontinuous value, among the projection data arranged in the order of sequence of said radiation beam detector elements array, to reassemble said noncontinuous data of discrete area with the data having said filtering undergone to provide the projection data for reconstructing said tomographic image.

2. An image reconstruction apparatus according to claim 1, wherein:

said noncontinuous data processing device includes:
a separator device for isolating any noncontinuous data in said discrete area from said projection data, converting said isolated noncontinuous projection data to continuous data so as for the value to change consistently, and serving only those continuous data for said filtering; and
a synthesizer device for synthesizing said continuous data derived from said filtering and said noncontinuous data of discrete area to reassemble the projection data to be provided to said image reconstruction device.

3. An image reconstruction apparatus according to claim 1, wherein:

said noncontinuous data processing device includes:
an extractor device, for extracting said discrete areas based on the difference between the projection data having said filtering undergo and the projection data not having said filtering undergo; and
a synthesizer device for substituting the extracted noncontinuous data of said discrete area in the projection data having said filtering undergo with the projection data not having the filtering to prepare the projection data to be provided to said image reconstructor device.

4. An image reconstruction apparatus according to claim 1, wherein:

said radiation beam is X-ray.

5. An image reconstruction method, which uses the projection data obtained by detecting the radiation beam transmitted through a subject with a plurality of radiation beam detector elements to reconstruct the tomographic image of said subject, comprising a step of:

performing a predetermined filtering to data except for any discrete area including data of noncontinuous value, among the projection data arranged in the order of sequence of said radiation beam detector elements array, to reassemble said noncontinuous data of discrete area with the data having said filtering undergone to provide the projection data for reconstructing said tomographic image.

6. An image reconstruction method according to claim 5, further comprising the steps of:

isolating any noncontinuous data in said discrete area from said projection data, converting said isolated noncontinuous projection data to continuous data so as for the value to change consistently, and serving only those continuous data for said filtering; and
synthesizing said continuous data derived from said filtering and said noncontinuous data of discrete area to reassemble the projection data to be provided to said image reconstruction.

7. An image reconstruction method according to claim 5, further comprising the steps of:

extracting said discrete areas based on the difference between the projection data having said filtering undergo and the projection data not having said filtering undergo; and substituting the extracted noncontinuous data of said discrete area in the projection data having said filtering undergo with the projection data not having the filtering to prepare the projection data to be provided to said image reconstruction.

8. An image reconstruction method according to claim 5, wherein:
said radiation beam is X-ray.

9. A radiographic tomography imaging apparatus, comprising:
a radiation detector, having a radiation emitter device and a plurality of radiation detector elements placed opposedly on the both sides of a subject; and
an image reconstruction apparatus, for reconstructing a tomographic image of said subject based on the projection data obtained by detecting the radiation transmitted through said subject by said plurality of radiation detector elements;
wherein:
said image reconstruction apparatus comprises a noncontinuous data processing device, for performing a predetermined filtering to data except for any discrete area including data of noncontinuous value, among the projection data arranged in the order of sequence of said radiation beam detector elements array, to reassemble said noncontinuous data of discrete area with the data having said filtering undergone to provide the projection data for reconstructing said tomographic image.

10. A radiographic tomography imaging apparatus, according to claim 9, wherein:
said noncontinuous data processing device includes:
a separator device for isolating any noncontinuous data in said discrete area from said projection data, converting said isolated noncontinuous projection data to continuous data so as for the value to change consistently, and serving only those continuous data for said filtering; and
a synthesizer device for synthesizing said continuous data derived from said filtering and said noncontinuous data of discrete area to reassemble the projection data to be provided to said image reconstruction device.

11. A radiographic tomography imaging apparatus, according to claim 9, wherein:
said noncontinuous data processing device includes:
an extractor device, for extracting said discrete areas based on the difference between the projection data having said filtering undergo and the projection data not having said filtering undergo; and
a synthesizer device for substituting the extracted noncontinuous data of said discrete area in the projection data having said filtering undergo with the projection data not having the filtering to prepare the projection data to be provided to said image reconstructor device.

12. A radiographic tomography imaging apparatus, according to claim 9, wherein:
said radiation emitter device includes an X-ray tube.

13. A radiographic tomography imaging apparatus, according to claim 12, further comprising:
a collimator for shaping the X-ray emitted from said X-ray tube into an X-ray beam of sector form.

14. A radiographic tomography imaging apparatus, according to claim 9, wherein:
said radiation detector device is composed of an array of a plurality of X-ray detector elements.

15. A radiographic tomography imaging apparatus according to claim 9, wherein:
said image reconstructor device uses the filtered back projection method.

16. A radiographic tomography imaging apparatus according to claim 14, wherein:
said radiation detector device is composed of a combination of scintillator and photodiode.

* * * * *